(12) United States Patent
Kumar et al.

(10) Patent No.: US 9,606,269 B2
(45) Date of Patent: Mar. 28, 2017

(54) FORWARD-IMAGING TUNABLE LENS SYSTEMS AND PROBES

(71) Applicant: Board of Regents, The University of Texas System, Austin, TX (US)

(72) Inventors: Karthik Kumar, Austin, TX (US); Jonathan C. Condit, Austin, TX (US); Nathaniel J. Kemp, Concord, MA (US); Thomas E. Milner, Austin, TX (US); Xiaojing Zhang, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/833,393

(22) Filed: Aug. 24, 2015

(65) Prior Publication Data

US 2016/0045116 A1 Feb. 18, 2016

Related U.S. Application Data

(63) Continuation of application No. 14/023,197, filed on Sep. 10, 2013, now Pat. No. 9,121,690, which is a
(Continued)

(51) Int. Cl.
| | |
|---|---|
| *G02B 3/12* | (2006.01) |
| *A61B 5/00* | (2006.01) |
| *B82Y 20/00* | (2011.01) |
| *G01N 21/47* | (2006.01) |
| *G02B 3/14* | (2006.01) |
| *G01B 11/02* | (2006.01) |

(Continued)

(52) U.S. Cl.
CPC .............. *G02B 3/12* (2013.01); *A61B 5/0066* (2013.01); *A61B 5/6852* (2013.01); *B82Y 20/00* (2013.01); *G01B 11/02* (2013.01); *G01N 21/4795* (2013.01); *G02B 3/14* (2013.01); *G02B 26/105* (2013.01); *A61B 5/0084* (2013.01); *A61B 2562/028* (2013.01); *A61B 2562/0233* (2013.01); *A61B 2562/0285* (2013.01); *A61B 2562/12* (2013.01); *G01B 9/02091* (2013.01); *G01B 2290/65* (2013.01); *G02B 26/0833* (2013.01); *G02B 2207/101* (2013.01); *G02B 2207/109* (2013.01)

(58) Field of Classification Search
CPC .................................... G02B 3/12; G02B 3/14
USPC .................................................. 359/665–667
See application file for complete search history.

(56) References Cited

U.S. PATENT DOCUMENTS 5,171,266 A * 12/1992 Wiley .................. A61F 2/1613
623/6.22
5,321,501 A 6/1994 Swanson et al. ............. 356/479
(Continued)

OTHER PUBLICATIONS

Kumar, et al. "High-reflectivity two-axis vertical combdrive microscanners for sub-cellular scale confocal imaging applications" *IEEE Int'l Conf. Optical MEMS* pp. 120-121 (2006).
(Continued)

*Primary Examiner* — Darryl J Collins
(74) *Attorney, Agent, or Firm* — J. Peter Paredes; David G. Rosenbaum; Rosenbaum IP, P.C.

(57) ABSTRACT

Provided herein are forward-imaging tunable lens systems and probes. A lens assembly is disclosed herein and comprises at least one tunable lens.

20 Claims, 9 Drawing Sheets

Related U.S. Application Data continuation of application No. 12/703,603, filed on Feb. 10, 2010, now Pat. No. 8,531,676, which is a continuation of application No. PCT/US2008/072805, filed on Aug. 11, 2008.

(60) Provisional application No. 60/955,255, filed on Aug. 10, 2007.

(51) Int. Cl.
*G02B 26/10* (2006.01)
*G01B 9/02* (2006.01)
*G02B 26/08* (2006.01)

(56) References Cited

U.S. PATENT DOCUMENTS

| | | | |
|---|---|---|---|
| 5,969,848 A | 10/1999 | Lee et al. | 359/298 |
| 6,005,706 A | 12/1999 | Hwang | 359/291 |
| 6,369,954 B1* | 4/2002 | Berge | A61B 1/0019 349/200 |
| 2001/0048784 A1 | 12/2001 | Behin et al. | 385/18 |
| 2003/0218793 A1 | 11/2003 | Soneda et al. | 359/291 |
| 2004/0160687 A1 | 8/2004 | Van Drieenhuizen et al. | 359/872 |
| 2004/0218877 A1 | 11/2004 | Xie | 385/93 |
| 2004/0245871 A1 | 12/2004 | Kim et al. | 310/75 |
| 2005/0036150 A1 | 2/2005 | Izatt et al. | 356/479 |
| 2005/0036196 A1 | 2/2005 | Barnea et al. | 359/291 |
| 2005/0182329 A1 | 8/2005 | Ostrovsky | 600/476 |
| 2005/0194650 A1 | 9/2005 | Hung | 257/414 |
| 2006/0195019 A1 | 8/2006 | Premachandran et al. | 600/300 |
| 2006/0232783 A1 | 10/2006 | Choma et al. | 358/479 |
| 2007/0015969 A1 | 1/2007 | Feldman et al. | 600/160 |
| 2007/0086017 A1 | 4/2007 | Buckland et al. | 356/497 |
| 2007/0165301 A1* | 7/2007 | Chen | G02B 3/14 359/362 |
| 2007/0233396 A1 | 10/2007 | Tearney et al. | 702/19 |
| 2009/0021823 A1* | 1/2009 | Heim | G02B 3/14 359/290 |
| 2009/0029494 A1 | 1/2009 | Tseng et al. | 438/27 |
| 2011/0303638 A1 | 12/2011 | Zhang et al. | 216/24 |

OTHER PUBLICATIONS

PCT International Search Report issued in corresponding foreign application, PCT/US2008/072805, pp. 1-4 (Oct. 22, 2008).

PCT Written Opinion issued in corresponding foreign application, PCT/US2008/072805, pp. 1-5 (Oct. 22, 2008).

* cited by examiner

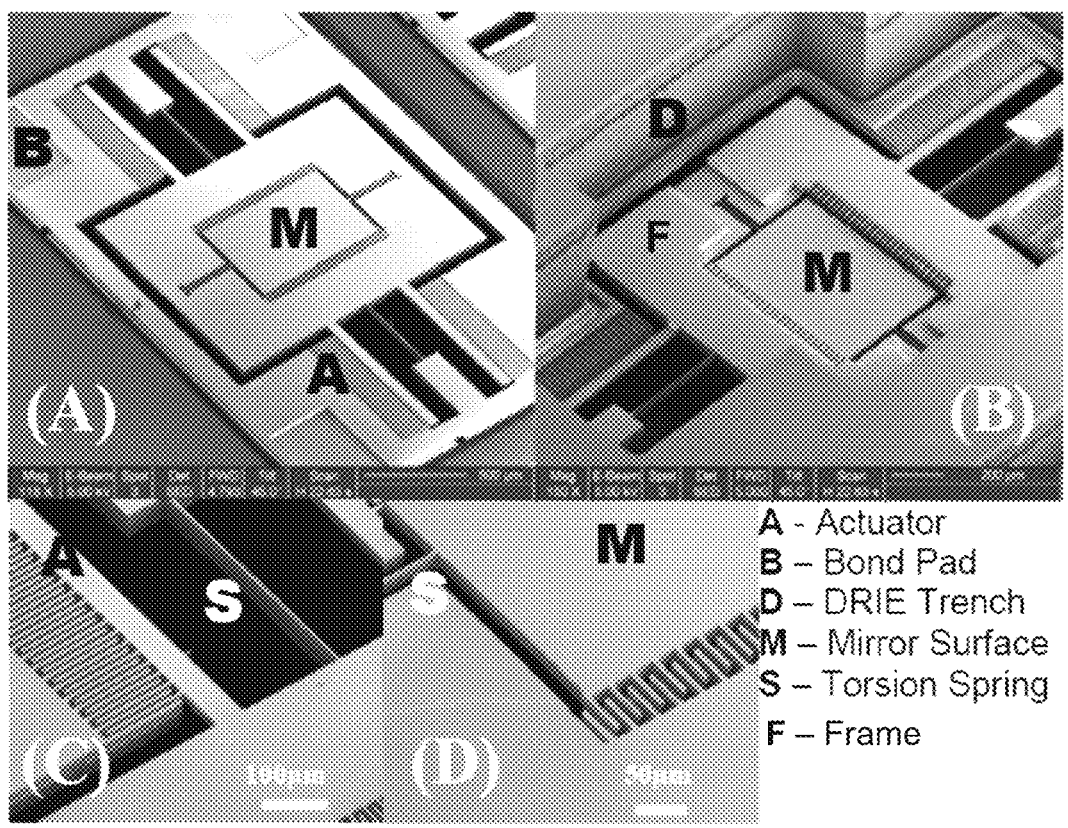
FIGS. 2A-D

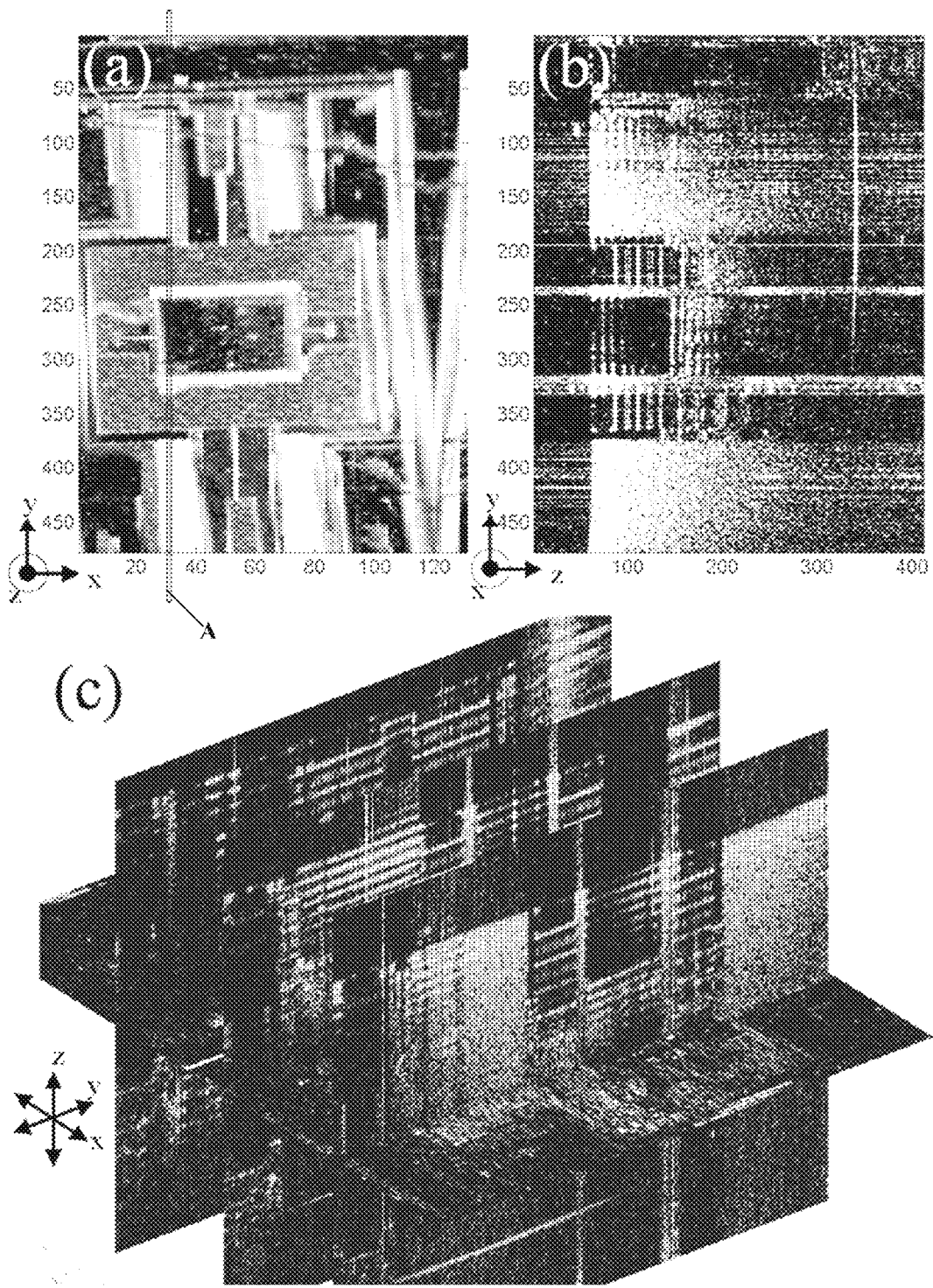
FIGS. 4A-C

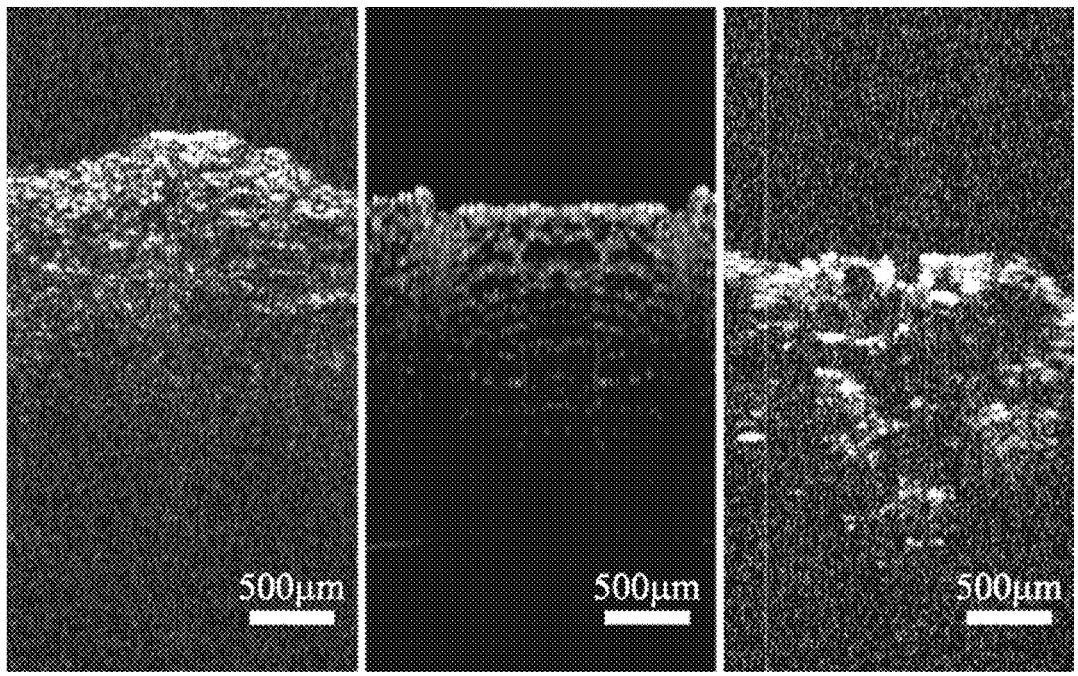
FIG. 4D　　　　　　　FIG. 4E　　　　　　　FIG. 4F
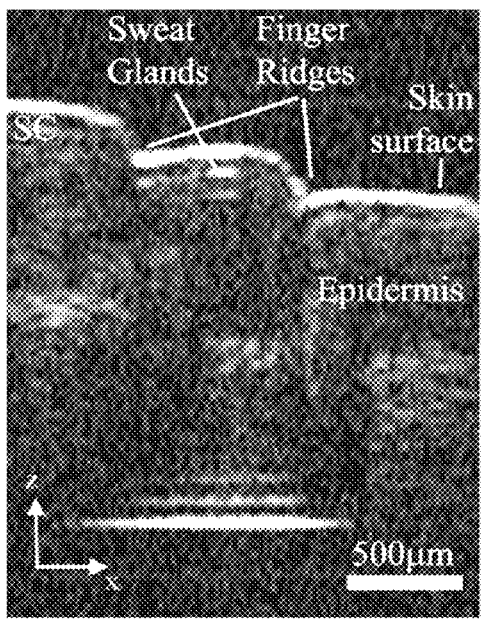 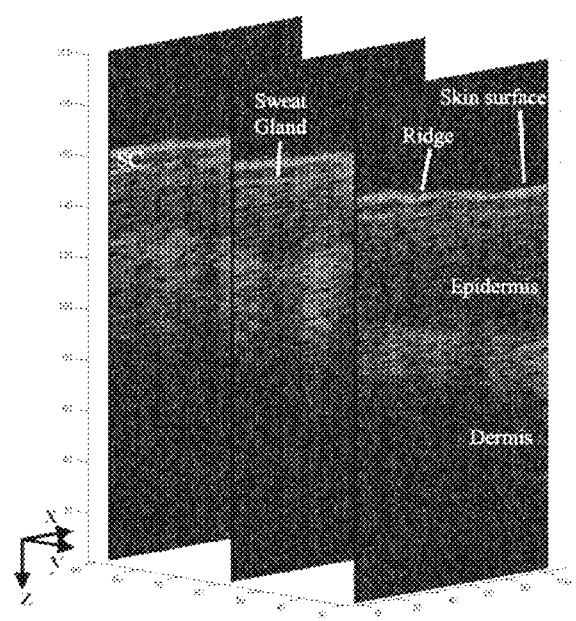
FIG. 4G　　　　　　　　　　　　FIG. 4H

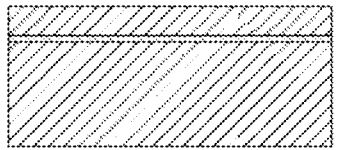

(A) SOI <100> 30μm device, 0.1-10Ωcm

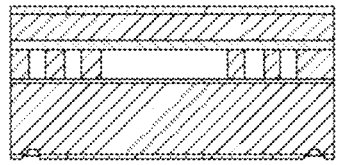

(D) Oxidize separate Si wafer, bond wafers, then grind/polish top layer to 20μm, LPCVD oxide

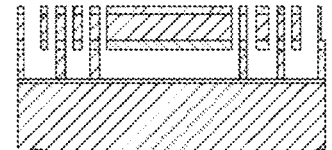

(G) RIE insulation oxide, DRIE etch to trim stator features to match rotors & create bond pad vias

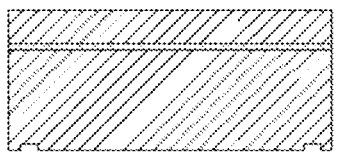

(B) Passivate surface (wet ox, 1100°C), make backside align marks

(E) DRIE expose front align marks, RIE oxide with bond pads & exact microscanner features

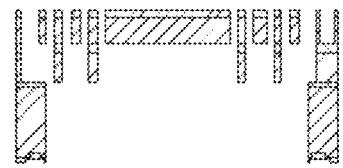

(H) Use backside align marks to create DRIE scanner release window

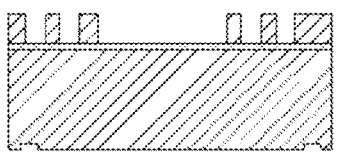

(C) BOE oxide, DRIE coarse stator features in silicon device layer

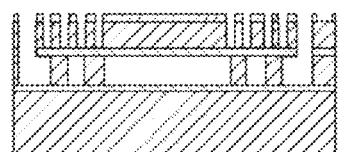

(F) DRIE etch top Si

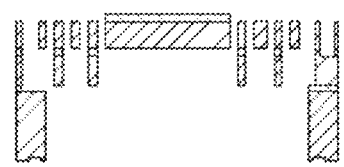

(I) Evaporate metal on mirror through mask

 Crystal Silicon    Thermal Oxide    LPCVD Oxide    Metal

FIGS. 7A-I

FORWARD-IMAGING TUNABLE LENS SYSTEMS AND PROBES

CROSS-REFERENCE TO RELATED APPLICATIONS

This application is a continuation of and claims priority to U.S. patent application Ser. No. 14/023,197, filed Sep. 10, 2013, now U.S. Pat. No. 9,121,690; which is a continuation of U.S. patent application Ser. No. 12/703,603, filed Feb. 10, 2010, now U.S. Pat. No. 8,531,676; which claims priority under 35 U.S.C. §365(c) to PCT International Application No. PCT/US2008/072805, filed Aug. 11, 2008, designating the United States; which claims priority to U.S. Provisional Application Ser. No. 60/955,255, filed Aug. 10, 2007, all incorporated by reference in the entirety herein.

BACKGROUND OF THE INVENTION

Optical coherence tomography (OCT) has emerged as a high-resolution diagnostic imaging tool. OCT is useful, for example, in cases where biopsy is difficult, for image-guided microsurgery, and for three-dimensional pathology reconstruction. Three dimensional OCT enhances visualization of morphology by providing tomographic and microscopic views simultaneously. Needed in the art are forward imaging OCT imaging systems and devices. Also needed are forward imaging OCT systems for intravascular and endoscopic use.

SUMMARY OF THE INVENTION

Provided are forward-imaging optical coherence tomography (OCT) systems and probes.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate alternative embodiments of the invention and together with the description, serve to explain the principles of the invention.

FIG. 2A shows a top view SEM image of an exemplary MEMS scanner for use in the exemplary system of FIG. 1A. FIG. 2B shows a bottom view SEM image of an exemplary MEMS scanner for use in the exemplary system of FIG. 1A. FIG. 2C shows an outer spring, comb bank SEM image of an exemplary MEMS scanner for use in the exemplary system of FIG. 1A. FIG. 2D shows an inner spring, comb bank SEM image of an exemplary MEMS scanner for use in the exemplary system of FIG. 1A.

FIG. 3A shows an exemplary frequency response curve and FIG. 3B shows an exemplary static single-sided voltage deflection curve.

FIGS. 4A-C shows SS-OCT Images using MEMS Scanner. FIG. 4A is an en face image of the scanner depicting mirror surface, torsion rods, bond pads, electrical bonding wires and subsurface inner stator comb features; FIG. 4B is a tomographic image of the scanning micromirror obtained at the location corresponding to the rectangle section A in FIG. 4A; FIG. 4C is slice images at different planes through the mircomirror device demonstrating volume image acquisition capability. FIGS. 4D-E are in vitro tomographic images of pickle slices obtained at 40 fps using the microscanner, and traditional galvanometric scanner, respectively (500 transverse pixels image); FIG. 4F is an in vitro tomographic image of onion peel obtained at 40 fps using microscanner; FIGS. 4G-H are in vivo images of human epidermis (finger) obtained at 20 fps, 40 fps (500 transverse pixels image), and FIG. 4H is tomographic slices of 3D volumetric image data, where each slice has a lateral extent of 1 mm (1 mm/100 pixels).

FIGS. 7A-I is the process flow for device fabrication in one embodiment of the MEMS scanner.

DETAILED DESCRIPTION

The present invention may be understood more readily by reference to the following detailed description of preferred embodiments of the invention and the Examples included therein and to the Figures and their previous and following description. Before the present systems, articles, devices, and/or methods are disclosed and described, it is to be understood that this invention is not limited to specific synthetic methods as such may vary. It is also to be understood that the terminology used herein is for the purpose of describing particular embodiments only and is not intended to be limiting.

As used in the specification and the appended claims, the singular forms "a", "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings: "Optional" or "optionally" means that the subsequently described event or circumstance may or may not occur, and that the description includes instances where said event or circumstance occurs and instances where it does not.

Reference will now be made in detail to the present preferred embodiment(s) of the invention, example(s) of which are illustrated in the accompanying drawings. Wherever possible, the same reference numbers are used throughout the drawings to refer to the same or like parts.

Figure 1A:
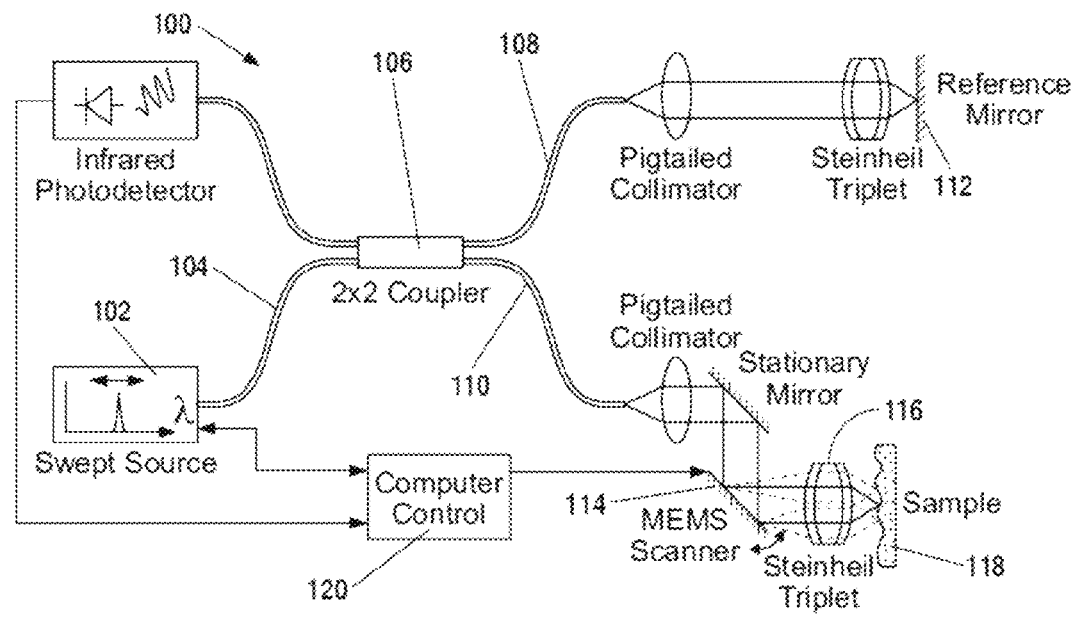
FIG. 1A is a schematic diagram of an exemplary forward-imaging SS-OCT system in accordance with one aspect of the invention.
Figure 1B:
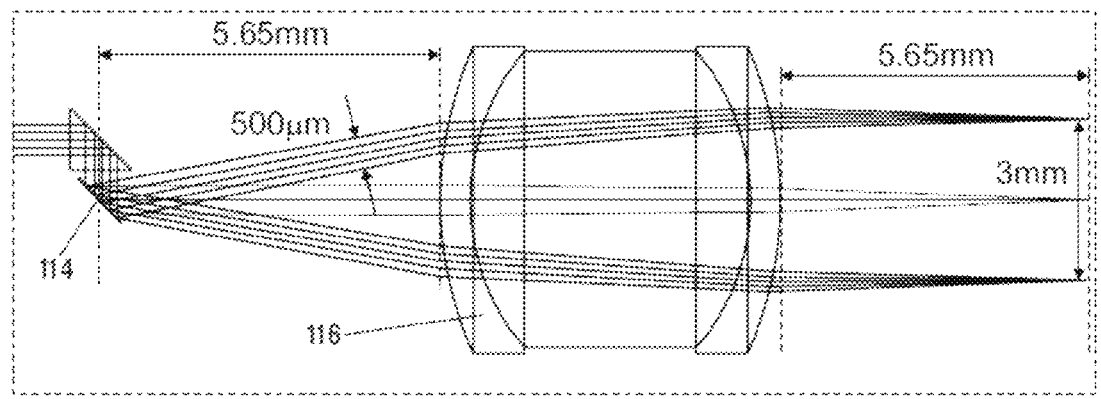
FIG. 1B is a schematic diagram further illustrating the optical characteristics of the exemplary forward-imaging SS-OCT system of FIG. 1A.
Figure 1C:
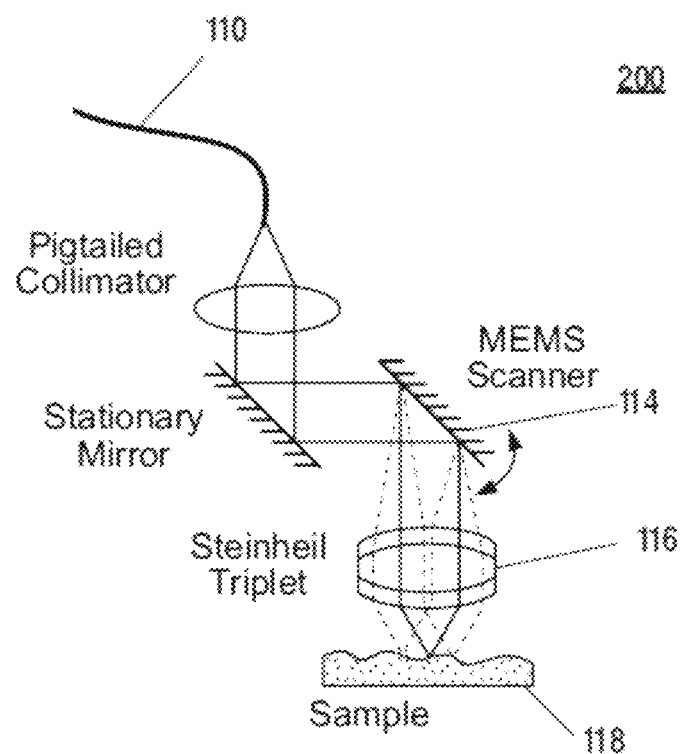
FIG. 1C is a schematic diagram further illustrating the system distal end of the exemplary forward-imaging SS-OCT system of FIG. 1A.

An exemplary forward-imaging optical coherence tomography (OCT) system 100 is shown in FIGS. 1A-C. In one aspect, light energy can be generated by a swept light source 102. Such a light source is also know as and can be referred to as a spectrally swept light source. For example, a swept light source may include, but is not limited to, a swept laser light source, a tunable superluminescent light emitting diode or tunable superluminescent diode, amplified spontaneous emission (ASE) sources that combine a broadband light source, typically a source that generates light by ASE, with tunable filters and amplifiers. If a swept light source is used, the system can be referred to as a swept source optical coherence tomography system or SS-OCT.

Optionally, the light source is a tunable laser. Optionally, the tunable laser has a power of about 10 mW, a center frequency of about 1310 nm, an about 100 nm range and can produce about 20,000 A-scan/second, theoretically providing $\lambda_c^2/2\Delta\lambda=8.6$ μm axial resolution and 4 mm imaging depth. Exemplary laser parameters are shown in Table 1:

TABLE 1

Exemplary Laser Parameters:

| | |
|---|---|
| $\lambda c$ | 1310 nm |
| $\Delta\lambda$ | 110 nm |
| Spectral Sweep Rate | 10 kHz or higher |
| $I_{avg}$ | 10 mW |

Laser devices meeting these operating parameters can be obtained, for example, from Santec (Hackensack, N.J.). In one aspect, the light source 102 can be a broadband laser light source coupled into optical fiber emitting light energy over a broad range of optical frequencies. The light energy can be emitted over a multiplicity of optical wavelengths or frequencies. As used herein, optical fiber can refer to glass or plastic wire or fiber. As one skilled in the art will appreciate, where light energy is described as "passing," "traveling," "returning," "directed," "transmitted," "directed" or similar movement, such movement can be via one or more optical fiber. Alternatively, the laser device is a Fourier Domain Mode Locking ("FDML") may be included as the laser source. In FDML, the spectrum, rather than the amplitude of the field, is modulated. A dynamic spectral window function (wavelength window which changes in time), rather than a temporal one (time window with no wavelength dependence), is applied. As a result, the laser generates a sequence of narrowband optical frequency sweeps at the cavity repetition rate or a harmonic thereof. Multiple tunable wavelength sources may included with, where each tunable wavelength source has a receiver, so each tunable wavelength source is coupled with a detector. The composite of all the tunable wavelength laser sources and detectors can act as very large bandwidth laser source. This frequency-swept output can also be thought of as a sequence of highly chirped, long pulses, with a fixed phase relationship between successive frequency sweeps.

As shown in FIG. 1A, Light from the light source can be directed to a coupler 106 and can be split into a reference path 108 and a sample path 110. Light energy directed into the reference path 108 can be reflected from a reference reflector surface 112 back to the coupler 106. The reference reflector can be, by way of example, but not limitation, a planar metallic mirror or a multilayer dielectric reflector with a specified spectral amplitude/phase reflectivity. In one aspect, a phase sensitive system can be used and a phase sensitive spectral domain OCT image can be produced. As would be clear to one skilled in the art, in a phase sensitive system the reference and sample light share a common path with the reference reflector positioned proximal to the sample.

The remaining fraction of light that entered the sample path 110 is reflected by a Microelectricmechanical system (MEMS) scanner 114 onto a target sample 118 for imaging. The MEMS scanner 114 may be referred to as a micromirror scanner, microscanner, or scanning reflector throughout this disclosure. As shown in FIG. 1B, light energy in the sample path can pass through a lens assembly 116 prior to contacting the sample 118. In one aspect, as shown in FIGS. 1A and 1C, the lens assembly 116 is operatively positioned between the scanner 114 and the sample 118. In this aspect, the scanning reflector 114 is located about the back focal plane of the lens assembly 116. In an alternative aspect, the MEMS scanner 114 can be operatively positioned between the lens assembly 116 and the sample. This is known to those skilled in the art as a post objective scanning configuration. Thus, in one aspect the lens assembly can be operatively positioned at the fiber tip before a MEMS scanner 114.

The scanner 114 and lens portions of the sample path can be operatively positioned within an OCT probe. The OCT probe can be located within a subject to allow light reflection off of subject tissues. The OCT probe can be sized for endoscopic or catheter placement within the subject. For example, the probe can be sized for insertion into an endoscopic port or opening, or for placement into and through a vessel of a subject for vascular applications. The diameter or largest cross-sectional dimension of the probe can be about 3 millimeters or less. For example, the diameter or largest cross-sectional dimension of the probe can be about 2 millimeters or less.

The MEMS scanner 114 can comprise a scanning reflector surface configured to be rotated about two axes in a single operating plane to direct light transmitted along the sample path 110 to the sample 118 to be imaged. In one aspect, the scanning reflector is a vertical comb-drive microscanner. In another aspect, the scanner or scanning reflector has a reflectivity of about 30% or greater. In other aspects, the reflectivity is 40%, 50%, 60%, 70%, 80%, 90%, 95% or greater. The reflective surface of the scanner can comprise silicon. The silicon can be coated with one or more layers of metallic or diaelectic coatings. For example, the coating is optionally metal. The metal can be selected from the group consisting of silver, gold and aluminum. Other reflective metals or layers can also be used. These layers can be coated on the surface using known methods in the art of optics, for example, electron beam evaporation or deposition can be used to coat the scanner.

Scanner rotation about two axes can be achieved by use of self-aligned vertical comb drive actuators. Decoupled two-axis rotation can be achieved by mounting the mirror and inner stator combs by torsion rods in a frame with gimbals in the orthogonal direction. Staggered vertical comb drives combine large scanning angles, high electrostatic actuating torque, favorable voltage pull-in characteristics, low mirror dynamic deformation under resonant operation, and optically smooth mirror surfaces. In an alternative embodiment, a scanner without gimbals can be used. In one aspect, mirrors can be fabricated with dimensions of 500 μm×700 μm to facilitate illumination at 45° incidence by 500 μm diameter laser beam, allowing for uncomplicated optical paths and integration into imaging systems. Exemplary steps of fabrication a scanner for use with the described forward-imaging OCT systems and probes is described below.

Fabrication can begin with protection of the Silicon-on-Insulator (SOI) 30 μm device layer surface by thermal oxidation, as generally shown in FIGS. 7A-I. With the front side surface protected by oxide, alignment marks can be dry etched into the backside of the wafer. Front side oxide can be removed and coarse features of mirror frame and outer stator combs, aligned to the backside alignment marks, can be etched into the device layer by Deep Reactive Ion Etching (DRIE). Thermal oxide of about 4800 Å thickness can be grown on a separate bare silicon wafer, which can then be fusion bonded on top of the of SOI wafer. Initial protection of SOI device layer by oxide can be used to achieve high yield in the fusion bonding process. After bonding, the top Si wafer can be ground to a thickness about 30 μm and polished to give smooth surface for optical interface. The mirror can be fabricated in this layer. For example, 1 μm of low temperature oxide (LTO) can be deposited on the front side of the wafer. Bond pad features can be defined by partially etching the LTO layer down to depth of 0.3 μm. The exact features of the stator and rotor combs of the microscanner can then be defined by etching through the LTO layer. Misalignment tolerance between these features and the coarse features defined in the SOI device layer during the critical backside alignment step can be given by half the comb gap spacing or 2.5 μm.

After patterning of LTO is complete, DRIE can be used to transfer the comb features of the microscanner to the upper (rotor) layer. This can followed by dry oxide etch to remove LTO oxide above the bond pads and etch the intermediate insulating layer simultaneously. DRIE can be used again to trim the coarse features in the SOI device layer to match the features in the upper layer.

After this self-alignment step, features of the microscanner are defined, and backside DRIE can be used to release the scanner. The device wafer can be bonded to a handle wafer by photoresist and backside DRIE of the outline of the microscanner can performed using the alignment marks previously etched into the backside of the device wafer. The device can be soaked in acetone for 12 hours to release device wafer from the handle wafer. Dry oxide etch can be performed on the front and back sides to remove exposed oxide from the mirror surfaces. E-beam evaporation can be used to coat a thin film (500-1000 Å) of aluminum on the mirror surface to improve reflectivity. The non-conformal nature of deposition combined with large step height can be taken advantage of to deposit metal on the mirror surface without electrically connecting the different layers.

In one aspect, a silicon wafer of <100> orientation can be coated with silicon nitride by Low Pressure Chemical Vapor Deposition. Rectangular openings of appropriate shape and size can be created in the silicon nitride layer by photolithography and reactive ion etching techniques commonly used in the semiconductor industry. The exposed silicon of the substrate can be preferentially etched anisotropically by potassium hydroxide solution to form a through-wafer hole. This though-wafer hole can then aligned over the micromirror of the microscanner by means of alignment marks created during the etch processes. Following hard mask alignment, the micromirrors can be selectively coated with 125 nm of silver (or any other material of choice and as described herein) by electron beam evaporation to improve mirror reflection characteristics. The MEMS scanner is shown in FIGS. 2A-D in the SEM micrographs depicting mirror (M) and frame design (F), torsion springs (T), actuator (A) including stator and rotor combs, bond pads (B) and backside DRIE trench release window (D) of the MEMS scanner.

By rotating the scanner surface about the two axes in a single operating plane, the sample can be scanned in an arbitrary raster pattern. Exemplary scanner characteristics are shown in Table 2:

TABLE 2

| Exemplary Mirror/Scanner Characteristics | |
|---|---|
| Mirror Size | 700 μm × 500 μm |
| Roughness | <100 nm RMS |
| Coating | 125 nm Silver |
| Reflectivity | ~95% (1260-1360 nm) |

Whether positioned proximal or distal to the scanner, the lens assembly 116 can comprise one or more lens. The lenses of the assembly can be static or tunable. Exemplary lens parameters are shown in Table 3:

TABLE 3

| Exemplary Objective Lens Parameters | |
|---|---|
| Manufacturer | JML Optical |
| NA | 0.6 |
| EFL | 7.9 mm or shorter |

In one aspect, the lens assembly comprises a combination of at least one static and at least one tunable lens. Optionally, the lens assembly can comprise a graded index lens. The lens assembly can also comprise a Steinheil triplet lens 116, which is schematically shown in FIGS. 1A-C. In one aspect, the lens assembly can comprise a lens with a field curvature that is less than about one wavelength of the light passing through the lens assembly.

If a tunable lens is used, it can comprise a deformable base material doped or coated with a plurality of nanoparticles. The deformable base material can be a gel, such as a sol gel, or a fluid, liquid or gas. The viscosity and density of the lens base material allows for control of surface changes in the lens when a field is applied. If surface tension, rather than a separate flexible film, is used to contain a liquid lens, then the surface tension properties can be used to provide a meniscus as the tunable lens. The applied force can cause the meniscus to become more or less round. Thus, the lens can have nanoparticles embedded or coated on the surface of the lens or distributed throughout the lens base material or body. The nanoparticles can be magnetized and can be moved by application of a magnetic or electric field to the lens. The movement of the nanoparticles can cause deformation of the lens, thus making it tunable.

Thus, a tunable microlens is an optical element whose optical power ($\phi$) may be tuned (varied) over a specified range ($\Delta\phi$) by applying a control signal. In one aspect, a magnetically activated tunable microlens can be used. In this approach, the optical power of an element can be varied by modifying the surface profile (h(r)) of a lens element. The surface profile (h(r)) can be modified by application of an external magnetic field that exerts a force on magnetized nanoparticles (longitudinal) or magnetic beads (radial) that are distributed in a controlled manner within the lens element.

Figure 5:
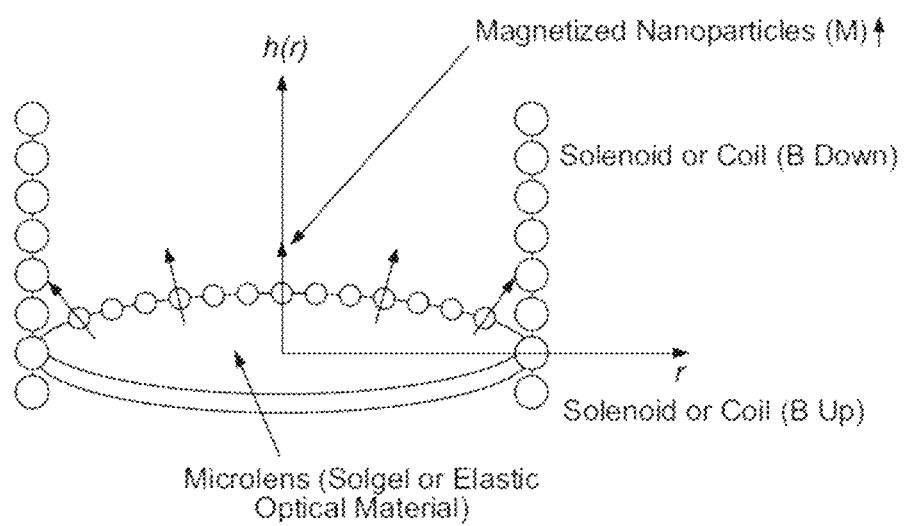
FIG. 5 is a schematic illustration showing longitudinal activation of a microlens in accordance with one aspect of the invention. Magnetic field gradient ($\nabla B$) can be provided by upper and lower solenoids acting on the magnetized nanoparticles positioned on the lens surface. Magnetic nanoparticles can be positioned on the surface of the microlens. Application of $\nabla B$ causes the surface profile (h(r)) to change and vary the optical power of the microlens.
Figure 6:
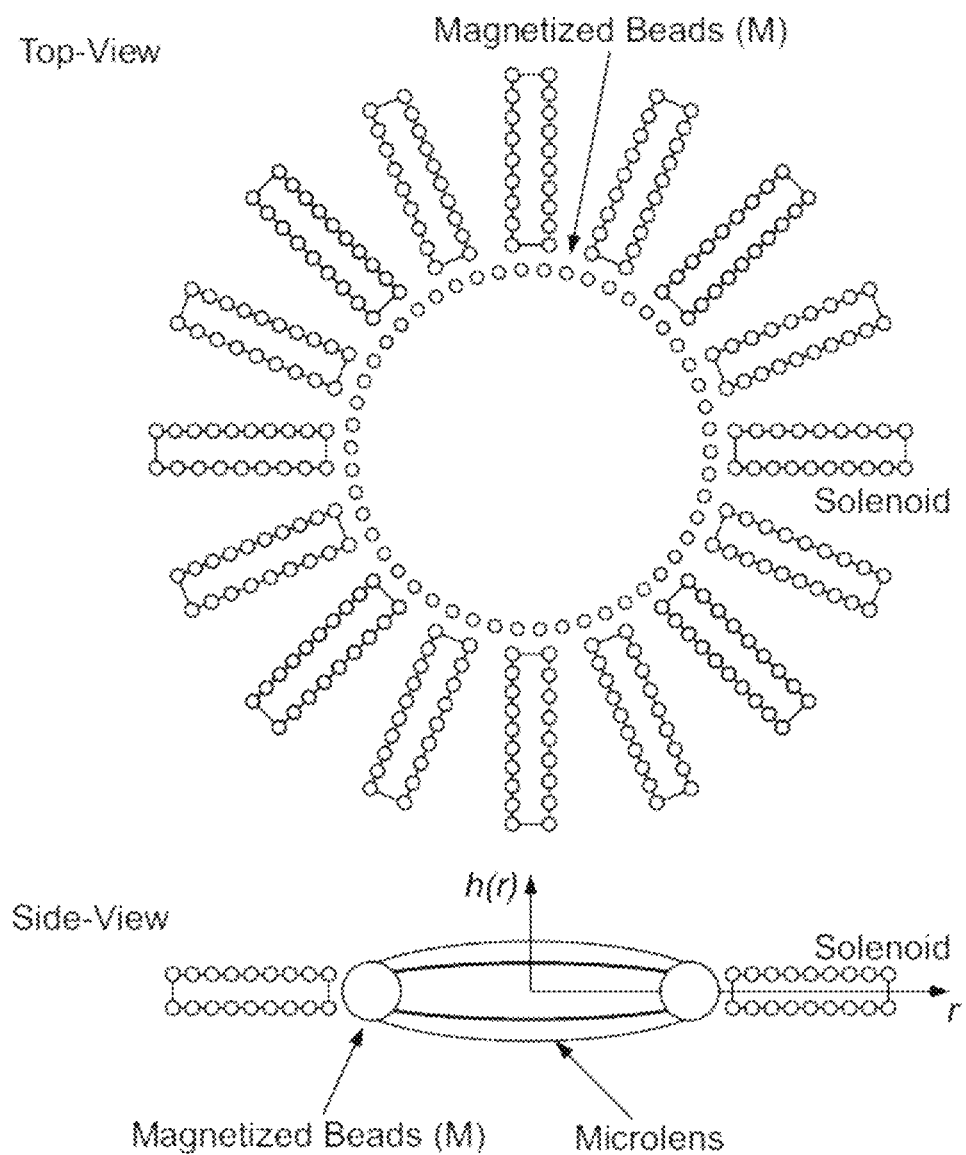
FIG. 6 is a schematic illustration showing radial activation of the microlens in accordance with one aspect of the invention. Magnetic field gradient ($\nabla B$) can provided by adjacent solenoids acting on the magnetized beads positioned in the rim of the lens. Application of $\nabla B$ causes the lens to radially stretch modifying the surface profile (h(r)) to change and vary the optical power of the microlens.

Actuation of the microlens can be achieved by varying the strength of an applied magnetic field gradient. Two exemplary and non-limiting representative geometries for a magnetic activated tunable microlens are entitled longitudinal activation (FIG. 5) and radial activation (FIG. 6).

Two solenoids with counter-circulating currents can be positioned longitudinally about the microlens so that the gradient of the magnetic field can be easily varied. Current in the solenoids can be provided using a push-pull arrangement so that the gradient of the magnetic field can be quickly and easily changed by decreasing or increasing current in one or both of the solenoids. The surface stress actuation ($\Sigma_\alpha$, Force/Area) on the microlens surface can be proportional to the vector product of the magnetic moment surface density ($M_s$) of the nanoparticles on the lens surface and the magnetic field gradient ($\nabla B$), as shown by Equation (1):

$$\Sigma_\alpha = (M_s \cdot \nabla) B \quad \text{(Eq.1)}$$

The magnetic nanoparticles (for example, $Fe_2O_3$, $Fe_3O_4$, Co, Mn, rare earth metals, or combinations thereof) can have a diameter sufficiently large (at least 10-20 nm) to maintain a permanent magnetic moment at an exemplary maximum temperature (300 K) of operation yet can be sufficiently small so that the nanoparticle diameter is at least ten times smaller than the wavelength of incident light in the microlens. Direction and strength of the magnetic moment of the nanoparticles can be varied according to surface location of the nanoparticles on the microlens.

The magnetic nanoparticles can be applied to the surface of the microlens by a spray, evaporation or similar process necessary to maintain a constant thickness commonly used for coating optical surfaces. Direction and strength of the magnetic moment of the magnetic nanoparticles can be fixed by applying a point-like magnetic field near the microlens surface for a fixed duration of time. Application of a point-like magnetic field can be used to fix the spatial orientation of the magnetic tinnoparticles (the nanoparticles can have a preexisting magnetic moment or the point-like magnetic field can induce a magnetic moment). Proceeding in this manner using fabrication procedures well known in the art, the magnitude and direction of the magnetic moment surface density ($M_s$) on the microlens surface can be prepared to a pre-determined specification.

Optical power of the microlens can be varied by applying a magnetic field Gradient ($\nabla B$) to the microlens surface ($M_s$) to activate a surface stress ($\Sigma_\alpha$). Activation of a specified surface stress ($\Sigma_\alpha$) can cause the surface profile (h(r)) of microlens to change thereby varying the optical power.

The microlens can also be activated by applying a force in the radial direction. For radial activation, magnetic beads can be positioned about the rim of the microlens and a radial array of solenoids can be positioned about the rim each with their long axis aligned in a radial direction. The solenoids can be electrically connected in series to maintain an equal current and magnetic field strength through all of the solenoids. The magnetic beads can be positioned in the rim of the lens so that the beads do not absorb or scatter any light in the incident beam. The magnetic beads can be magnetized so that the magnetic moment of the beads is directed radially outward and parallel to the radius of the microlens. In comparison to longitudinal activation, magnetic beads may not be smaller than the wavelength of incident light but can be larger than 20 nm to maintain a constant magnetic moment at the maximum operating temperature of the microlens.

The linear stress actuation ($\Sigma_l$ Force/length) on the microlens rim can be proportional to the vector product of the magnetic moment line density ($M_l$) of magnetic beads on the lens rim and the magnetic field gradient ($\nabla B$), as shown in Equation (2):

$$\Sigma_l = (M_l \cdot \nabla) B \quad \text{(Eq.2)}$$

The magnetic beads ($Fe_2O_3$, $Fe_3O_4$, Co, Mn or combinations thereof) can be embedded in a ring structure that mechanically forms the rim of the microlens. The ring structure can be formed from a variety of elastic materials including thermoplastics or polymers that can be molded or machined. The magnetic beads can be imbedded in the ring structure and can be magnetized by applying a point-like magnetic field ring surface for a fixed duration of time. Direction of the magnetic moment of the beads in the ring structure can he aligned radially outward along the axis of the microlens.

Optical power of the microlens can be varied by applying a magnetic field gradient ($\nabla B$) to the rim of the microlens ($M_l$) to activate a linear stress ($\Sigma_l$) in a radial direction along the rim of the lens. The magnitude of the magnetic field gradient ($\nabla B$) can be varied by the current in the solenoids positioned around the lens. Activation of a specified linear stress ($\Sigma_l$) causes the surface profile (h(r)) of microlens to change thereby varying the optical power.

Referring again to FIG. 1, the light energy that entered the sample path 110 can be reflected off of the sample tissue. The reflected light energy passes back through the sample path 110 and the reflected sample path light and reflected reference path 108 light can recombine either constructively or destructively, depending on the difference of path lengths. A series of constructive and destructive combinations of reflected light can be used to create an interferogram (a plot of detector response as a function of optical path length difference ($c\tau$) or optical time-delay ($\tau$)). Each reflecting interface from the subject can generate an interferogram. The Fourier transform of the spectral interference signal provides a map of the reflectivity profile of the sample as a function of depth. The two axis MEMS scanning micromirror moves the beam spot laterally in two dimensions and the axial reflectivity profiling is performed at each point to develop a 3D image of the sample volume.

The reflected light can be placed in operative communication with a processing or computing system which can process data to produce an OCT image. The produced OCT image in one aspect is a phase sensitive spectral domain OCT image. The scanner and laser source can also be controlled by the computing system 120. Exemplary imaging parameters for the described forward imaging OCT system include those shown in Table 4:

TABLE 4

| Exemplary Imaging Parameters | |
|---|---|
| Lateral Resolution | $0.61 \times \lambda_c \times f/D = 12.6$ μm |
| Axial Resolution | $\lambda_c^2 / 2\Delta\lambda = 8.6$ μm |
| Field of View | $2 \times 1 \times 4$ mm$^3$ |
| Axial Points per A-scan | 465 |
| Laser A-scan Rate | 20,000 scans/sec |
| Volume Pixel (Voxel) Imaging Rate | 9.3 million/sec |
| 2-D Imaging Rate | 20 kHz/500 = 40 fps (500 transverse pixels per image) |

Thus, in one exemplary aspect, a forward-imaging optical coherence tomography (OCT) system can comprise a light source and a light splitter in operative communication with the light source. The splitter can be configured to split light from the light source for transmission along a reference path and a sample path. The reference path can comprise a reference reflector surface. The sample path can comprise a scanning reflector surface configured to be rotated about two axes in a single operating plane to direct light transmitted along the sample path to a sample to be imaged. The system can further comprise a processing or computing system in operative communication with the reference and sample paths for processing light energy reflected from the reference reflector and sample to produce an OCT image of the sample.

The processor or computing system can include, but are not limited to, one or more processors or processing units, a system memory, and a system bus that couples various system components including the processor to the system memory.

The system bus represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus, and all buses specified in this description can also be implemented over a wired or wireless network connection and each of the subsystems, including the processor, a mass storage device, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer can include a variety of computer readable media. Such media can be any available media that is accessible by the computer and includes both volatile and non-volatile media, removable and non-removable media. The system memory includes computer readable media in the form of volatile memory, such as random access memory (RAM), and/or non-volatile memory, such as read only memory (ROM). The system memory 112 typically contains data such as data and/or program modules such as operating system 105 and application software that are immediately accessible to and/or are presently operated on by the processing unit.

The computer can also include other removable/non-removable, volatile/nonvolatile computer storage media. A mass storage device can provide non-volatile storage of computer code, computer readable instructions, data structures, program modules, and other data for the computer. For example, a mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device, including by way of example, an operating system and application software. Each of the operating system and application software (or some combination thereof) can include elements of the programming and the application software. Data can also be stored on the mass storage device. Data can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer via an input device. Examples of such input devices include, but are not limited to, a keyboard, pointing device (e.g., a "mouse"), a microphone, a joystick, a serial port, a scanner, and the like. These and other input devices can be connected to the processing unit via a human machine interface that is coupled to the system bus, but may be connected by other interface and bus structures, such as a parallel port, game port, or a universal serial bus (USB). In an exemplary system of an embodiment according to the present invention, the user interface can be chosen from one or more of the input devices listed above. Optionally, the user interface can also include various control devices such as toggle switches, sliders, variable resistors and other user interface devices known in the art. The user interface can be connected to the processing unit.

A display device can also be connected to the system bus via an interface, such as a display adapter. For example, a display device can be a monitor or an LCD (Liquid Crystal Display). In addition to the display device, other output peripheral devices can include components such as speakers and a printer which can be connected to the computer via Input/Output Interface.

The computer can operate in a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet. The remote computer can be a server, a router, a peer device or other common network node, and typically includes all or many of the elements already described for the computer. In a networked environment, program modules and data may be stored on the remote computer. The logical connections include a LAN and a WAN. Other connection methods may be used, and networks may include such things as the "world wide web" or Internet.

Computer readable media can be any available media that can be accessed by a computer. By way of example, and not limitation, computer readable media can comprise "computer storage media" and "communications media." Computer storage media include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method can be stored on or transmitted across some form of computer readable media.

The processing of the disclosed methods and the processing performed by the disclosed system can be performed using software components. The disclosed systems and devices can include computer-executable instructions, such as program modules, being executed by one or more computers or other devices. Generally, program modules include computer code, routines, programs, objects, components, data structures, etc. that perfixm particular tasks or implement particular abstract data types. The disclosed systems and devices can also be used with grid-based and distributed computing environments where tasks are performed by remote processing devices that are linked through a communications network. In a distributed computing environment, program modules may be located in both local and remote computer storage media including memory storage devices.

Aspects of the exemplary systems and devices shown in the Figures and described herein, can be implemented in various forms including hardware, software, and a combination thereof. The hardware implementation can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), field programmable gate array(s) (FPGA), etc. The software comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

Aspects of the exemplary systems can be implemented in computerized systems. Aspects of the exemplary systems, including for instance the computing unit, can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

Aspects of the exemplary systems can be described in the general context of computer instructions, such as program modules, being executed by a computer. Generally, program modules include routines, programs, objects, components, data structures, etc. that perform particular tasks or implement particular abstract data types.

In one aspect, the OCT system is phase sensitive. In another aspect, the phase sensitive system has a swept light source. The reflected light energy can processed to provide a three-dimensional OCT image of the sample. The reflected light energy can also be processed to provide a time-domain, Doppler or Fourier Domain OCT image.

Also provided is an OCT probe for use with an OCT imaging system. A forward imaging OCT probe can comprise a scanning reflector surface configured to be rotated about two axes in a single operating plane to direct light transmitted along an OCT sample path to a sample to be imaged. The OCT imaging probe can further comprise a lens assembly as described herein. The lens assembly can be operatively positioned between the scanning reflector surface and the sample. Thus, the scanning reflector surface can be located about the back focal plane of the lens assembly. In another aspect, the scanning reflector can be operatively positioned between the lens assembly and the sample.

The OCT imaging probe can be configured for endoscopic operation within a human or animal subject. For example, the lens assembly and the scanning reflector surface are operatively positioned within a housing sized for insertion into the subject through an endoscopic port or opening. In one aspect, the diameter or largest cross-sectional dimension of the housing is about 3 millimeters or less. Optionally, the diameter or largest cross-sectional dimension of the housing is about 2 millimeters or less.

EXAMPLES

The following examples are put forth so as to provide those of ordinary skill in the art with a complete disclosure and description of how the systems, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Miniaturization of optical diagnostic equipment is important for translation of OCT techniques from research laboratories to clinical medicine. Micro-electromechanical system (MEMS) technologies were used to package micro-optical elements with actuators for imaging in in vivo environments. Swept Source OCT (SS-OCT) can be used for real-time high-resolution imaging due to continual improvements in laser wavelength scan range, line width, and scan speed.

Described in this example is a miniature forward-looking Swept Source OCT system incorporating a silver-coated silicon MEMS scanner for high-speed 3-D volumetric imaging. The silicon MEMS scanner provides two-dimensional angular scanning of incident broadband light using silver-coated surfaces in a common plane.

A forward-imaging configuration was used for the fiber-based OCT system (FIG. 1A). The described system can be miniaturized into an OCT endoscope. The forward-imaging OCT endoscopes can be used for image-guided surgery in sensitive tissues including the gastrointestinal (GI) tract, breast, liver, and ovaries, cardiovascular system, brain, urinary, and reproductive systems. In one aspect, the exemplary system utilizes a tunable laser (10 mW, 1310 nm $\lambda$ center, 110 nm range, 20,000 A-scans/sec, Santec), and a Steinheil triplet lens (JML Optical TRP14340/100, 0.6 NA, 7.9 Mm EFL) to provide aberration-free focus of broadband illumination.

Optical design software (ZEMAX) simulation (FIG. 1B) demonstrated that a 500 µm diameter beam deflected by ±10° (optical) by a microscanner placed at the back focal plane of the triplet objective lens produced an approximately 3 mm linear scan and resulting in a beam spot size of approximately 12.5 µm on the sample. Therefore, adopting fiber-fused GRIN lenses and right-angle micro-prisms with micro-objectives enabled OCT endoscopes for 3-D imaging in many typically-inaccessible human organs. The two-axis microscanners (FIG. 2) can be fabricated by the process described above, and as described in Kumar et. al., "High-Reflectivity Two-Axis Vertical Combdrive Microscanners for Sub-cellular Scale Confocal Imaging Applications," IEEE Int'l Conf. Optical MEMS, 120-121 (2006). For example, the two-axis microscanner can have a 500 µm×700 µm mirror dimensions for 45° incident illumination. 125 nm-thick silver coating resulted in ~95% uniform reflectance over the source spectrum. As shown in FIGS. 2A-D, the MEMS scanner is that two-dimensional scanning can be obtained with a single plane device, where the mirror is suspended within a frame by the inner torsion springs aligned in the orthogonal direction, which enables two-dimensional rotation about a single pivot point, reducing optical field distortions. The MEMS scanner includes a mirror and frame design, torsion springs, an actuator including stator and rotor combs, bond pads, and backside DRIE release window. The mircomirror torsion springs, electrical bond pads and a 20 µm diameter bonding wire connecting to the top left bond pad, are clearly visible from the en face image. The subsurface stator combs for the inner rotation axis are also visible in the image, as evidenced by comparison with the scanning electron micrograph in FIG. 2A. FIG. 4C depicts tomographic cross-sectional slices across different positions of the micromirror, revealing the internal structural details of the device. The vertical comb drives cause large amounts of laser light scattering, leading to the grainy portions in the image, similar to speckle noise. The mirror section of the device is dark as it scatters very little of the incident light due to high transmission of silicon at infrared wavelengths.

Figure 3A:
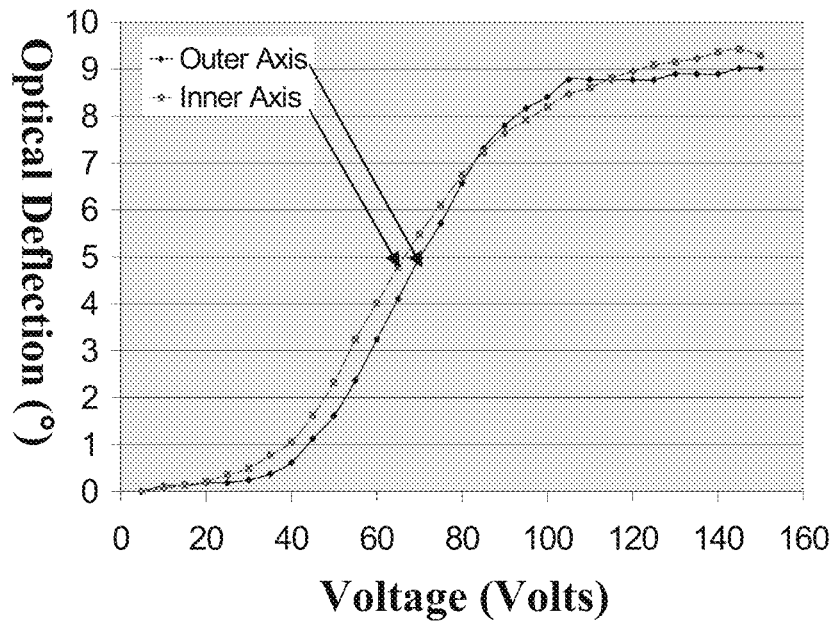
FIGS. 3A-B is graphs of the MEMS microscanner operating characteristics.
Figure 3B:
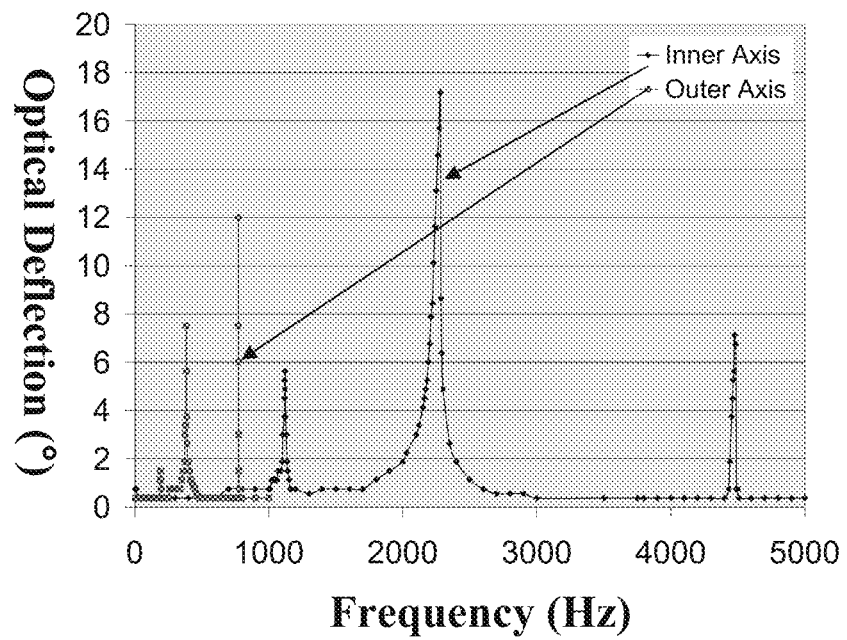

Inner and outer axis resonance at 2.28 kHz and 385 Hz (FIG. 3A) were observed, respectively, and 9° optical deflection on both axes for single-sided voltage input of 110 V at low frequencies (FIG. 3B) was also observed. Secondary peaks are also observed at half and twice the actual resonant frequency of the vibration modeshape. Due to the highly capacitive nature of the electrostatic actuators, the micromirror actuation requires very low current (usually of the order of 1-10 nA) for operation in non-resonant mode and around 2.4 µA in resonant mode on either axis. In one embodiment, voltage (V) applied to one vertical comb drive on each rotation axis is $V=18.0+9.0 \sin(2\pi f t)V$.

Tomographic images of in vitro biological samples at 40 frames $s^{-1}$ (for 2D imaging with 500 transverse pixels per image) by operating the scanning micromirror about only one axis of rotation. FIGS. 4D-F presents tomographic images of pickle slices obtained using the scanning micromirror and a traditional galvanometric scanner from different regions of the sample, and an onion peel using the micromirror. Subsurface morphology is visible in all the images.

Real-time 3D images of in vivo human finger skin using our system. Tomographic slices through the imaged volume are shown in FIGS. 4G-H. The micron-scale tissue architecture including skin surface, finger ridges, sweat glands, stratum corneum, epidermis and dermis are clearly visible in the slice images. In some of the images, lens flare artefacts are visible, but these can be repositioned away from the imaging region of interest by varying the path length difference between the sample surface and reference reflection.

The lateral and axial resolutions of the instrument are governed by independent factors. The axial resolution is inversely proportional to the spectral bandwidth of the swept-frequency laser. The lateral resolution is determined purely by the micromirror and scanning optics. The diameter of the scanning micromirror limits the maximum beam diameter incident on the objective lens, and therefore determines the effective numerical aperture of the focusing lens. The number of resolvable points of the system can be improved by increasing the product of the mirror diameter—scanning angle product, which is then transformed into a given lateral field of view and resolution, depending on the numerical aperture of the objective, which can be selected according to the requirements of the application. Some instability in lateral scanning was observed, which can be countered by incorporation of angular position feedback sensors on the scanning micromirror chip for adaptive control of scan linearity. Miniaturization of the MEMS scanning optics with the use of fiber-fused graded index (GRIN) lens collimators, stationary microprisms and monolithic electronics integration such as flipchip bonding for power supply and signal conditioning enables possible clinical application of the instrument for applications such as gastroenterology, urinary/reproductive tract and pulmonary imaging that allow catheter diameters of 5 mm. Real-time in vivo volume image acquisition of subsurface morphology at micrometer resolution may enable application to minimally invasive disease diagnostics, image-guided biopsy and photodynamic therapy.

FIGS. 7A-I is one process for the steps in fabricating the micromirror.

The scanning micro-optical system and high-speed broad-spectrum swept laser allowed imaging of $2\times1\times4$ mm$^3$ volume with $12.5\times12.5\times10$ µm resolution at 8 million voxels/sec. For 3D imaging, the system acquisition rate of over 10 million volume pixels per second results in the completion of one entire volume scan in approximately 15 s, representing an order of magnitude improvement in acquisition rate over time-domain OCT.

Microscanner structure and biological samples were clearly visible from the tomographic and en face views. Higher-than-video-rate (40 fps) in vivo acquisition of B-scans at micron resolution allow real-time monitoring of sub-surface morphology for disease diagnostics and image-guided biopsy and therapy. Swept Source three-dimensional OCT was demonstrated using a miniaturized forward-imaging probe incorporating a two-axis silicon microscanner. Tomographic, en face views of $2\times1\times4$ mm$^3$ volume with $12.5\times12.5\times10$ µm resolution were acquired at 8 million voxels/sec. Further miniaturization of the MEMS scanning optics, with the use of fiber-fused GRIN lens collimators, enables clinical applications of these catheters for diagnosis of the cardiovascular stenosis.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A lens assembly comprising at least one tunable lens, wherein the tunable lens includes an outer rim and a plurality of magnetic beads positioned only about the outer rim so that the magnetic moment of the plurality of magnetic beads are directed radially outward and parallel to the radius of the tunable lens and the plurality of magnetic beads do not absorb or scatter any light in an incident beam disposed on the tunable lens, wherein the tunable lens includes a longitudinal axis and a plurality of magnetic nanoparticles positioned only along the longitudinal axis.

2. The lens assembly as claimed in claim 1, wherein the lens assembly comprises a radial array of solenoids positioned about the outer rim of the tunable lens and the radial array of solenoids include a longitudinal axis that is aligned in a radial direction with respect to the outer rim.

3. The lens assembly as claimed in claim 1, wherein the lens assembly is operatively positioned within a probe sized for insertion into a subject through an endoscopic port or opening.

4. The lens assembly as claimed in claim 1, wherein the plurality of magnetic beads are selected from the group consisting of: $Fe_2O_3$, $Fe_3O_4$, Co, Mn, and combinations thereof.

5. The lens assembly as claimed in claim 4, wherein the tunable lens includes a deformable base material selected from the group consisting of a fluid, liquid, gel, and gas.

6. The lens assembly as claimed in claim 4, wherein the magnetic beads are embedded in a ring structure about the outer rim and the ring structure mechanically forms the outer rim of the tunable lens.

7. The lens assembly as claimed in claim 6, wherein the array of solenoids apply an magnetic field gradient to the outer rim as to activate a linear stress in a radial direction along the outer rim of the tunable lens.

8. A lens assembly comprising at least one tunable lens, wherein the tunable lens includes a longitudinal axis and a plurality of magnetic nanoparticles positioned only along the longitudinal axis.

9. The lens assembly as claimed in claim 8, further comprising at least two solenoids positioned around the tunable lens as to provide a push-pull arrangement.

10. The lens assembly as claimed in claim 9, wherein surface stress actuation ($\Sigma_\alpha$,Force/Area) on the tunable lens surface is proportional to the vector product of the magnetic moment surface density ($M_s$) of the plurality of magnetic nanoparticles on the tunable lens surface and the magnetic field gradient ($\nabla B$).

11. The lens assembly as claimed in claim 10, wherein the magnetic nanoparticles are selected from the group consisting of $Fe_2O_3$, $Fe_3O_4$, Co, Mn, rare earth metals, and combinations thereof.

12. The lens assembly as claimed in claim 11, wherein the at least two solenoids apply a magnetic field Gradient ($\nabla B$) to a microlens surface ($M_s$) to activate a surface stress ($\Sigma_\alpha$) to cause the surface profile (h(r)) of the tunable microlens to change and varying the optical power disposed through the tunable lens.

13. The lens assembly as claimed in claim 12, wherein the lens assembly is operatively positioned within a probe sized for insertion into a subject through an endoscopic port or opening.

14. A method for manufacturing a tunable lens of claim 8 comprising:
   forming an oxide layer on a front side of a first wafer;
   etching alignment marks on a backside of the first wafer;
   removing the layer of oxide from the front side of the first wafer;
   forming mirror frame features and outer stator comb features aligned to the backside alignment marks;
   etching the mirror frame features and the outer stator comb features;
   forming a thermal oxide layer on a second silicon wafer;
   fusing the second wafer to the front side of the first wafer;
   forming a mirror, rotor combs, and stator combs on a top side of the fused second silicon wafer;
   etching the backside of the first wafer to release the scanner using the backside alignment marks; and
   depositing a thin-film of a reflective material on a mirror surface.

15. The method of claim 14 where the step of etching the mirror frame features and the outer stator comb features is performed using Deep Reactive Ion Etching ("DRIE").

16. The method of claim 14 where the step of forming the thermal oxide layer on the second silicon wafer includes growing the thermal oxide to a thickness of 4800 Angstroms.

17. The method of claim 14 where the step of forming the mirror, rotor combs, and stator combs includes etching coarse features corresponding to the mirror, rotor combs, and stator combs aligned to the backside alignment marks into the fused second wafer using DRIE.

18. The method of claim 17 where the step of forming the mirror, rotor combs, and stator combs includes:
   depositing a low temperature oxide ("LTO") on the top side of the fused second wafer;
   etching the LTO to define the stator and rotor combs on the LTO layer; and
   DRIE etching the fused second wafer to form stator and rotor combs in the fused second wafer.

19. The method of claim 18 where the step of depositing the LTO includes depositing a 1 μm of LTO, and the step of etching the LTO includes:
   partially etching the LTO down to a depth of 0.3 μm to form bond pads;
   where the step of etching the LTO to define the stator and rotor combs on the LTO layer includes using the bond pads to define exact features for the stator and rotor combs.

20. The method of claim 19 further comprising:
   dry oxide etching the top side of the second wafer to remove the LTO from the bond pads and etch an intermediate insulating layer.

* * * * *